(12) United States Patent
Lin et al.

(10) Patent No.: US 8,889,106 B2
(45) Date of Patent: Nov. 18, 2014

(54) NON-ALCOHOL MOUTHWASH COMPOSITION WITHOUT CHEMICAL ANTIBACTERIAL MEDICAMENT

(71) Applicants: Feng-Huei Lin, Guishan Township, Taoyuan County (TW); Chun-Pin Lin, Taipei (TW); Hsuan-Yu Chen, Taichung (TW); Tzu-Piao Tang, Taipei (TW); Hsu-Wei Fang, Taipei (TW); Chung-King Hsu, Taipei (TW); Chia-Ming Chang, Taichung (TW)

(72) Inventors: Feng-Huei Lin, Guishan Township, Taoyuan County (TW); Chun-Pin Lin, Taipei (TW); Hsuan-Yu Chen, Taichung (TW); Tzu-Piao Tang, Taipei (TW); Hsu-Wei Fang, Taipei (TW); Chung-King Hsu, Taipei (TW); Chia-Ming Chang, Taichung (TW)

( * ) Notice: Subject to any disclaimer, the term of this patent is extended or adjusted under 35 U.S.C. 154(b) by 0 days.

(21) Appl. No.: 13/931,153

(22) Filed: Jun. 28, 2013

(65) Prior Publication Data
US 2014/0314687 A1 Oct. 23, 2014

(30) Foreign Application Priority Data
Apr. 23, 2013 (TW) .............................. 102207414 U

(51) Int. Cl.
*A61K 8/66* (2006.01)
*A61K 8/96* (2006.01)
*A61K 38/00* (2006.01)
*A61K 51/00* (2006.01)
*A61Q 11/00* (2006.01)
*A61K 8/92* (2006.01)

(52) U.S. Cl.
CPC .. *A61K 8/92* (2013.01); *A61Q 11/00* (2013.01)
USPC ................................. 424/54; 424/49; 424/50

(58) Field of Classification Search
USPC .......................................................... 424/50
See application file for complete search history.

(56) References Cited

U.S. PATENT DOCUMENTS 4,645,662 A * 2/1987 Nakashima et al. ............ 424/52
7,910,089 B2 * 3/2011 Uotani et al. ................... 424/50

* cited by examiner

*Primary Examiner* — Walter Webb
(74) *Attorney, Agent, or Firm* — Morris, Manning & Martin, LLP; Tim Tingkang Xia, Esq.

(57) ABSTRACT

A non-alcohol mouthwash composition without chemical antibacterial medicament is disclosed. The non-alcohol mouthwash composition includes from 0.03% to 1.5% of γ-polyglutamic acid (γ-PGA) and from 0.5% to 4% of surfactant, all percentages based on the total weight of the mouthwash composition. The non-alcohol mouthwash composition preferably includes from 0.4% to 1.5% by weight, or more preferably from 0.8% to 1.3% by weight, of γ-PGA. Containing no chemical antibacterial medicament, the non-alcohol mouthwash composition can effectively inhibit bacterial growth in the oral cavity without irritating the oral mucosa.

5 Claims, 6 Drawing Sheets

NON-ALCOHOL MOUTHWASH COMPOSITION WITHOUT CHEMICAL ANTIBACTERIAL MEDICAMENT

BACKGROUND OF THE INVENTION

1. Technical Field

The present invention relates to a mouthwash composition and, more particularly, to a non-alcohol mouthwash composition without chemical antibacterial medicament.

2. Description of Related Art

The oral cavity is in daily contact with food and therefore becomes a hotbed for bacteria. In fact, there are more than six hundred species of bacteria known to be found in the oral cavity, including *Capnocytophaga sputigena*, *Lactobacillus brevis*, *Staphylococcus aureus*, *Streptococcus mutans*, *Staphylococcus oralis*, *Escherichia coli*, *Pseudomonas aeruginosa*, and *Staphylococcus thermophiles*, to name only a few, and some of the bacteria tend to cause dental caries, periodontal diseases, or other common oral diseases. However, tooth brushing can clean only 50% of the tooth surface; the remainder depends on dental floss and mouthwash for cleaning.

The conventional mouthwash ingredients include alcohol and synthetic chemical compositions such as chlorhexidine (CHX) or cetylpyridinium chloride (CPC). Therefore, a conventional mouthwash not only can make teeth yellow, which is esthetically undesirable, but also irritates the oral mucosa, which is especially unacceptable to one who is receiving chemo- or radiotherapy in the head or neck area, and whose oral mucosa is often inflamed and vulnerable as a result of the therapy. While mouthwash is essential for maintaining the oral hygiene of such patients, the aforesaid mouthwash ingredients are simply too irritant to their sensitive oral mucosa.

In addition, the alcohol in mouthwash is liable for white lesions of the oral mucosa and may influence the alcohol content measurement in a breath test (which is conducted as a part of, or an alternative to, a field sobriety test), making mouthwash an inappropriate oral hygiene product for those who have to drive immediately after use. A mouthwash composition is therefore needed which can inhibit bacterial growth in the oral cavity without irritating the oral mucosa and which is suitable for use before driving.

BRIEF SUMMARY OF THE INVENTION

The present invention provides a non-alcohol mouthwash composition without chemical antibacterial medicament. The mouthwash composition includes γ-polyglutamic acid (γ-PGA) and a surfactant, wherein γ-PGA makes up from 0.03% to 1.5%, preferably from 0.4% to 1.5%, and more preferably from 0.8% to 1.3%, of the total weight of the mouthwash composition. The present invention can effectively inhibit bacterial growth in the oral cavity without injuring the oral mucosa.

The present invention provides a non-alcohol mouthwash composition without chemical antibacterial medicament, comprising: γ-polyglutamic acid (γ-PGA) making up from 0.03% to 1.5% of a total weight of the mouthwash composition; and a surfactant making up from 0.5% to 4% of the total weight of the mouthwash composition.

Implementation of the present invention at least achieves the following advantageous effects:

1. Effectively inhibiting bacterial growth in the oral cavity;
2. Causing no harm to the oral mucosa; and
3. Having no influence on breath test results.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1A:
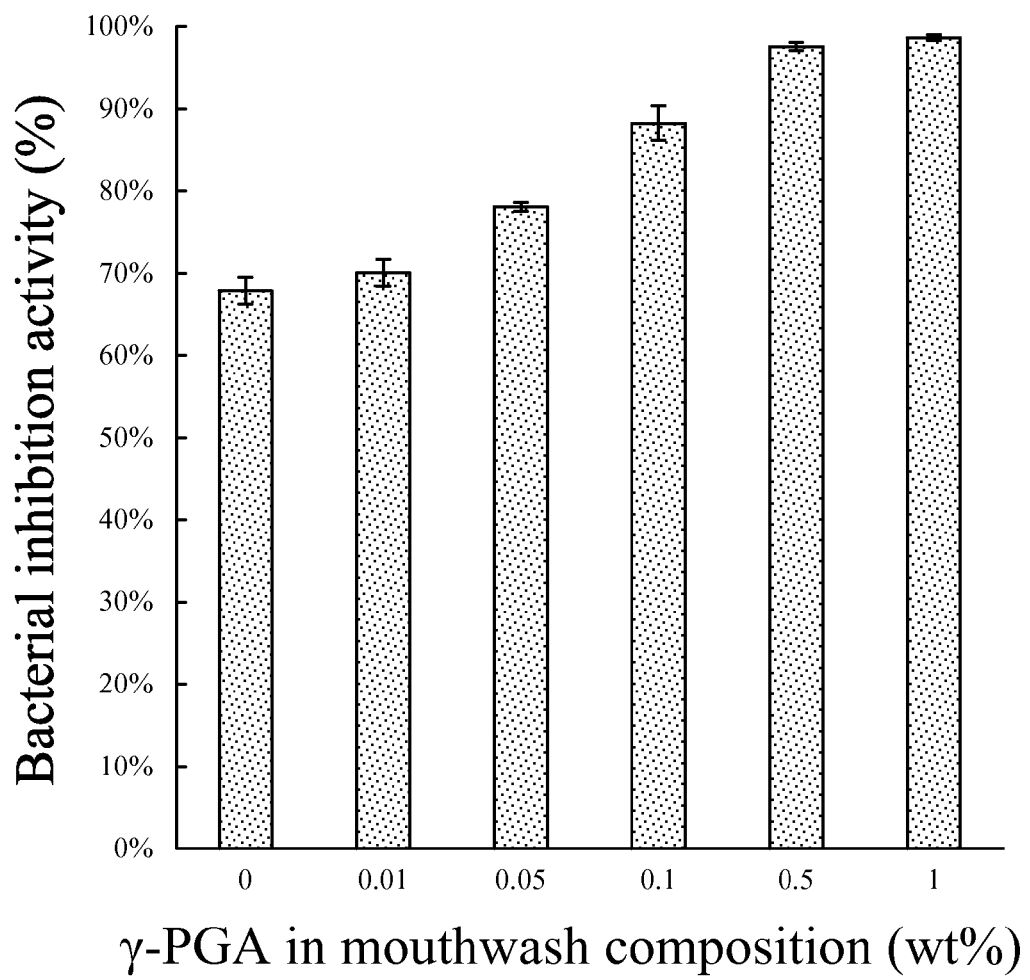
FIG. 1A is a bar chart based on densitometric measurements, showing the bacterial inhibition activities of the mouthwash compositions in an embodiment of the present invention, wherein the mouthwash compositions have different concentrations of γ-PGA and are reacted with *Escherichia coli*.

In an embodiment of the present invention, a non-alcohol mouthwash composition without chemical antibacterial medicament includes γ-polyglutamic acid (γ-PGA) and a surfactant.

γ-PGA was first found in 1973 in the cell walls of *Bacillus anthracia* and is a novel natural polymer which can be synthesized by microbial fermentation (e.g., with the *Bacillus subtilis* natto variety of *Bacillus subtilis*). γ-PGA advantageously features non-toxicity, high biocompatibility, biodegradability, bacterial inhibition activity, moisture retention ability, adsorptivity, and low acquisition cost.

Due to the aforesaid advantageous features, γ-PGA is applicable to tackifiers and stabilizers in the food industry, heavy metal adsorbents for water treatment, humectants in the chemical industry, soil conditioners for use in agriculture, and nutrition supplements in the health food industry. In particular, the microbe-inhibiting and food-grade features have made γ-PGA a newly popular material in the food, cosmetic, and biomedical material industry. The present embodiment, therefore, uses γ-PGA as a bacterial inhibitor in the mouthwash composition.

The mouthwash composition includes from 0.03% to 1.5% of γ-PGA (based on the total weight of the mouthwash composition) in lieu of the irritant chemical compositions commonly used in commercially available mouthwash compositions, with a view to enhancing oral hygiene and health. Preferably, γ-PGA makes up from 0.4% to 1.5% of the total weight of the mouthwash composition. More preferably, γ-PGA makes up from 0.8% to 1.3% of the total weight of the mouthwash composition. The higher the γ-PGA content is, the more effective the mouthwash composition will be in terms of bacterial inhibition. However, excessively high γ-PGA content will make the mouthwash composition tacky, which is an undesirable feel in the mouth as far as mouthwash is concerned.

The surfactant, which constitutes from 0.5% to 4% of the total weight of the mouthwash composition, serves to blend the oleophilic components and hydrophilic components of the mouthwash composition together, thereby increasing the uniformity of the mouthwash composition. Preferably, the surfactant makes up from 2% to 3% of the total weight of the mouthwash composition. The surfactant may be glycerol, and the concentration of glycerol may range from 95 wt % to 99 wt %, or preferably is 95 wt %, of the surfactant.

The non-alcohol mouthwash composition without chemical antibacterial medicament may further include potassium nitrate, which makes up from 0.001% to 3% of the total weight of the mouthwash composition. Potassium nitrate can release potassium ions, and free potassium ions are capable of blocking nerve conduction and thereby reducing pain. In other words, potassium nitrate can provide temporary relief to the symptoms of sensitive teeth.

The non-alcohol mouthwash composition without chemical antibacterial medicament may further include chlorhexidine gluconate, which makes up from 0.001% to 0.1% of the total weight of the mouthwash composition. Chlorhexidine gluconate is a common bacterial inhibitor but tends to irritate the oral mucosa if used excessively. Since the non-alcohol mouthwash composition without chemical antibacterial medicament already contains the bacteria-inhibiting γ-PGA, only a tiny amount of chlorhexidine gluconate is needed to enhance bacterial inhibition. A tiny amount of chlorhexidine gluconate will not cause irritation to the oral mucosa.

The non-alcohol mouthwash composition without chemical antibacterial medicament may further include a perfume, which makes up from 0.05% to 0.3% of the total weight of the mouthwash composition. The perfume may be a spearmint essential oil, a peppermint essential oil, or a combination of both. The perfume is intended to enhance the smell of the mouthwash composition or its feel in the mouth. For example, a spearmint essential oil can add to the pleasant smell of the mouthwash composition, while a peppermint essential oil can give the mouthwash composition a refreshing taste in the mouth. A spearmint essential oil may constitute from 0.1% to 0.2% of the total weight of the mouthwash composition.

The non-alcohol mouthwash composition without chemical antibacterial medicament may further include an edible colorant, such as Brilliant Blue FCF. Without a colorant, a mouthwash is hardly visually distinguishable from plain water, so an edible colorant may be added to the non-alcohol mouthwash composition without chemical antibacterial medicament to make it easily distinguishable. The concentration of Brilliant Blue FCF is usually 2.5 mg/L.

To verify the effectiveness in bacterial inhibition of the non-alcohol mouthwash composition with γ-PGA but without chemical antibacterial medicament, bacterial inhibition tests were conducted using standard strains of *Escherichia coli* (ATCC 23815), *Staphylococcus aureus* (ATCC 10832), and *Pseudomonas aeruginosa* (ATCC 10145). The reaction time of the tests was set at eight hours because, according to the growth curves of the three standard strains, each of these strains can reach the exponential growth phase after about eight hours.

The non-alcohol mouthwash composition without chemical antibacterial medicament was prepared in the following manner. More specifically, a total of five such compositions were prepared, each having a different weight percentage of γ-PGA:

Experimental group 1: 100 mg of γ-PGA powder, 744 μL it of spearmint essential oil, 20 mL of glycerol (in 99.5% concentration), and 2.5 mg of Brilliant Blue FCF (CI.42090) were added into 1 L of water and stirred until evenly mixed. Therein, γ-PGA made up 0.01% of the total weight of the mouthwash composition.

Experimental group 2: 500 mg of γ-PGA powder, 744 μL of spearmint essential oil, 20 mL of glycerol (in 99.5% concentration), and 2.5 mg of Brilliant Blue FCF (CI.42090) were added into 1 L of water and stirred until evenly mixed. Therein, γ-PGA made up 0.05% of the total weight of the mouthwash composition.

Experimental group 3: 1,000 mg of γ-PGA powder, 744 μL of spearmint essential oil, 20 mL of glycerol (in 99.5% concentration), and 2.5 mg of Brilliant Blue FCF (CI.42090) were added into 1 L of water and stirred until evenly mixed. Therein, γ-PGA made up 0.1% of the total weight of the mouthwash composition.

Experimental group 4: 5,000 mg of γ-PGA powder, 744 μL of spearmint essential oil, 20 mL of glycerol (in 99.5% concentration), and 2.5 mg of Brilliant Blue FCF (CI.42090) were added into 1 L of water and stirred until evenly mixed. Therein, γ-PGA made up 0.5% of the total weight of the mouthwash composition.

Experimental group 5: 10,000 mg of γ-PGA powder, 744 μL of spearmint essential oil, 20 mL of glycerol (in 99.5% concentration), and 2.5 mg of Brilliant Blue FCF (CI.42090) were added into 1 L of water and stirred until evenly mixed. Therein, γ-PGA made up 1% of the total weight of the mouthwash composition.

In a laminar flow cabinet, 9 mL was taken from each of the five mouthwash compositions (experimental groups 1~5), a commercially available product A (experimental group 6), a commercially available product B (experimental group 7), a commercially available product C (experimental group 8), and a normal saline (control group). Each 9-mL sample was injected into a sterilized glass test tube. Following that, 1 mL of *Escherichia coli* solution (with an optical density (O.D.) of 0.1 and a colony density of $10^6$ CFU/mL) was added into each sterilized glass test tube and mixed well for densitometric measurement. To perform colony-forming unit counting experiments, samples were taken from the glass test tubes and, after dilution, spread on solid culture media respectively. All the glass test tubes and solid culture media were placed in a thermostatic incubator of 37° C. for eight hours, before the absorbance (or optical density) of each glass test tube and the number of colony-forming units in each Petri dish were measured.

Based on the densitometric measurements, bacterial inhibition activity was calculated by dividing the difference between the after-culture absorbance of the control group and the after-culture absorbance of an experimental group with the after-culture absorbance of the control group. Based on the results of the colony-forming unit counting experiments, on the other hand, bacterial inhibition activity was calculated by dividing the difference between the number of colony-forming units of the control group and the number of colony-forming units of an experimental group with the number of colony-forming units of the control group. The bacterial inhibition activities thus obtained were plotted into charts. After the experiments with *Escherichia coli* were completed, the same experiments were repeated for *Staphylococcus aureus* and *Pseudomonas aeruginosa* respectively in order to obtain and plot the bacterial inhibition activities toward *Staphylococcus aureus* and toward *Pseudomonas aeruginosa*.

Figure 1B:
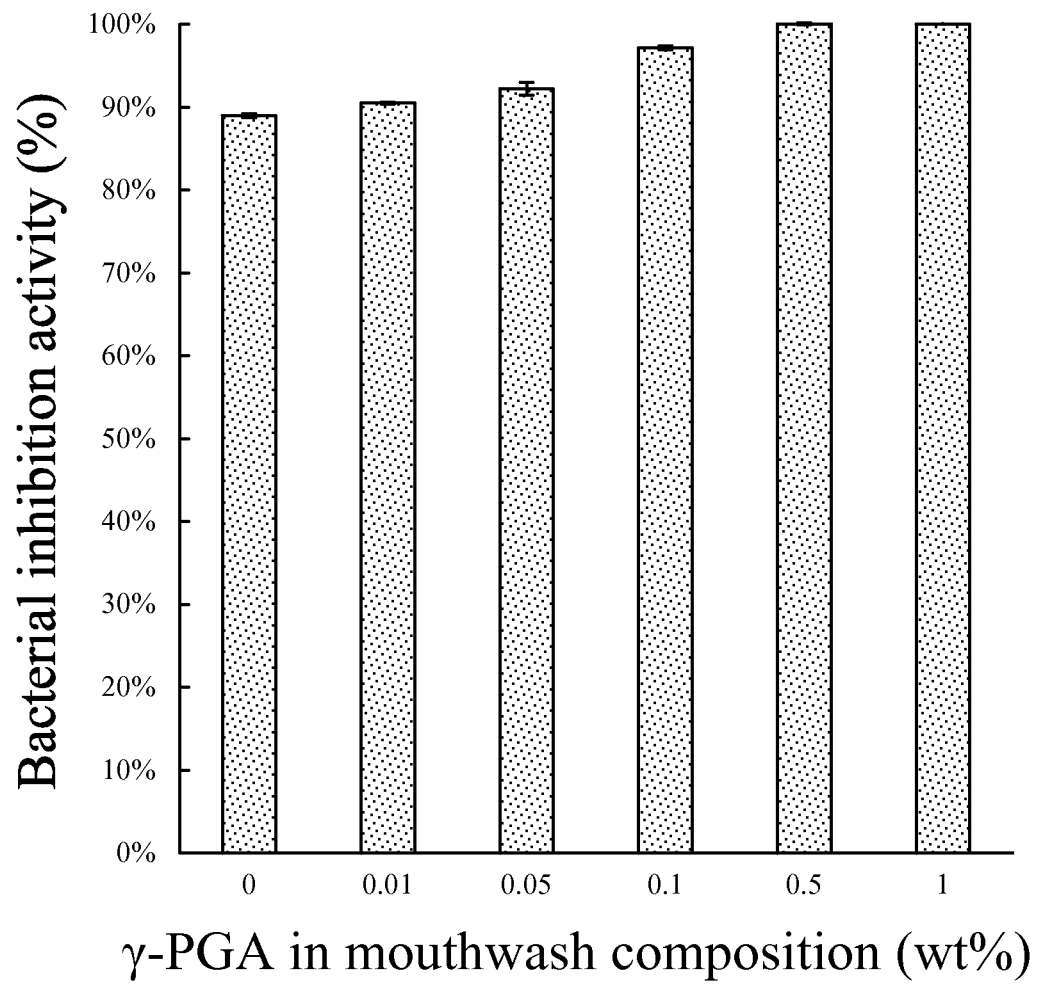
FIG. 1B is a bar chart based on the results of colony-forming unit counting experiments, showing the bacterial inhibition activities of the mouthwash compositions in an embodiment of the present invention, wherein the mouthwash compositions have different concentrations of γ-PGA and are reacted with *Escherichia coli*.

Please refer to FIG. 1A and FIG. 1B for the experiment results with regard to *Escherichia coli*. Both the densitometric measurements and colony-forming unit counting experiments show that, among the five non-alcohol mouthwash compositions without chemical antibacterial medicament (experimental groups 1~5), the mouthwash compositions of experimental group 4 (containing 0.5 wt % of γ-PGA) and experimental group 5 (containing 1 wt % of γ-PGA) exhibited bacterial inhibition activities higher than 90%. Experimental groups 4 and 5, which show the higher bacterial inhibition activities, are further compared with the commercially available mouthwash compositions as follows.

Table 1 shows the bacterial inhibition activities of experimental groups 4 to 8 toward *Escherichia coli* as determined by densitometry. Table 2 shows the bacterial inhibition activities of experimental groups 4 to 8 toward *Escherichia coli* as determined by the colony-forming unit counting experiments. As shown in Table 1 and Table 2, the bacterial inhibition activities of the mouthwash compositions of experimental groups 4 and 5 are comparable to those of the commercially available products A, B, and C containing irritant chemicals, i.e., all higher than 95%.

TABLE 1

| Experimental group | 4 | 5 | 6 | 7 | 8 |
|---|---|---|---|---|---|
| Bacterial inhibition activity (%) | 97.44 | 98.28 | 97.13 | 98.51 | 97.36 |

TABLE 2

| Experimental group | 4 | 5 | 6 | 7 | 8 |
|---|---|---|---|---|---|
| Bacterial inhibition activity (%) | 99.99 | 99.99 | 99.99 | 99.99 | 99.99 |

Figure 2A:
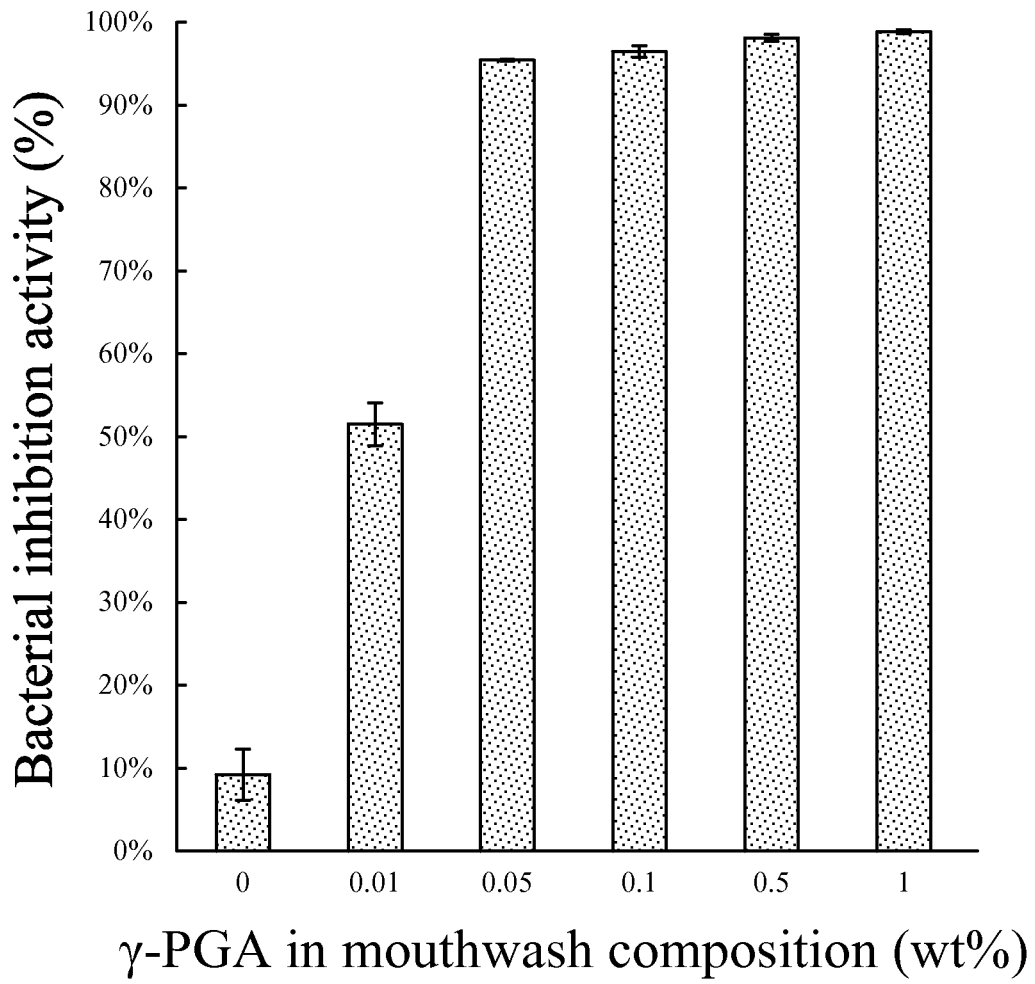
FIG. 2A is a bar chart based on densitometric measurements, showing the bacterial inhibition activities of the mouthwash compositions in an embodiment of the present invention, wherein the mouthwash compositions have different concentrations of γ-PGA and are reacted with *Staphylococcus aureus*.
Figure 2B:
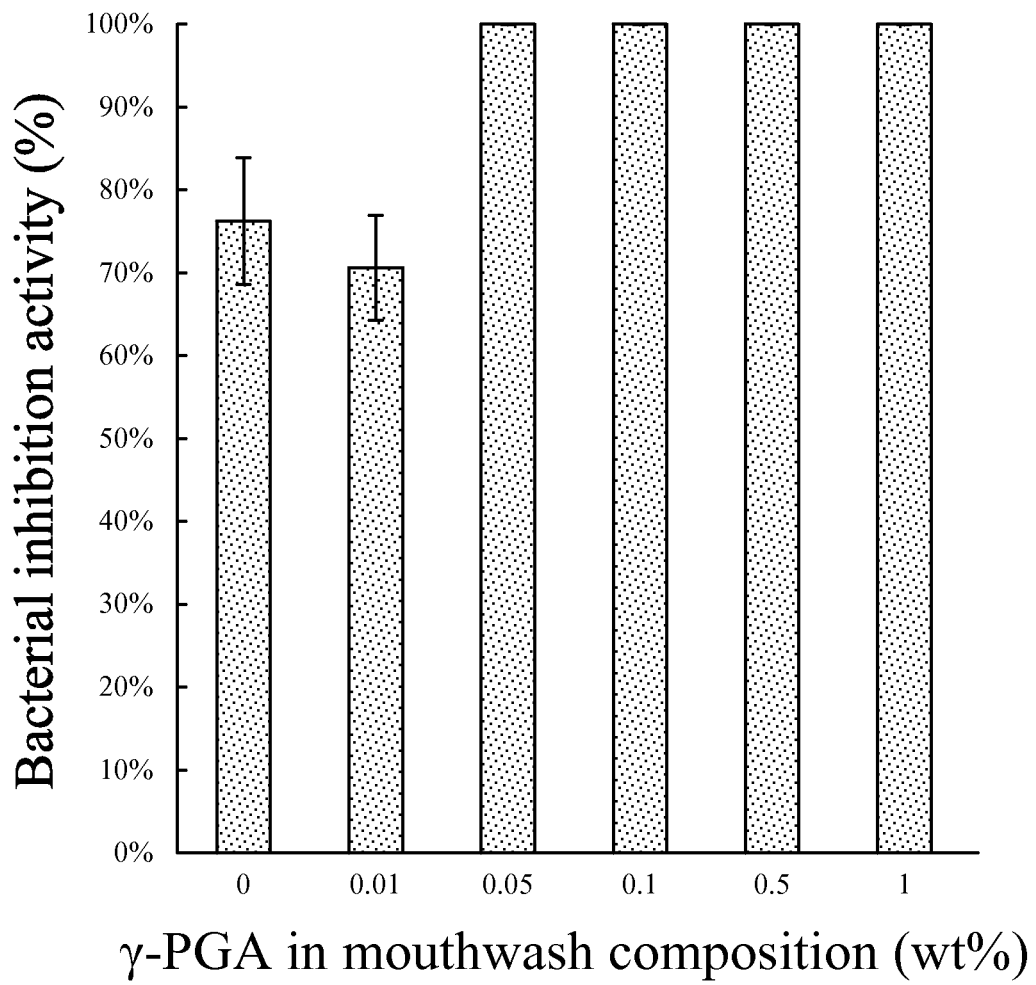
FIG. 2B is a bar chart based on the results of colony-forming unit counting experiments, showing the bacterial inhibition activities of the mouthwash compositions in an embodiment of the present invention, wherein the mouthwash compositions have different concentrations of γ-PGA and are reacted with *Staphylococcus aureus*.

Reference is now made to FIG. 2A and FIG. 2B for the experiment results with regard to *Staphylococcus aureus*. Both the densitometric measurements and colony-forming unit counting experiments show that, among the five non-alcohol mouthwash compositions without chemical antibacterial medicament (experimental groups 1~5), the mouthwash compositions of experimental group 2 (containing 0.05 wt % of γ-PGA), experimental group 3 (containing 0.1 wt % of γ-PGA), experimental group 4 (containing 0.5 wt % of γ-PGA), and experimental group 5 (containing 1 wt % of γ-PGA) exhibited bacterial inhibition activities higher than 90%.

Table 3 shows the bacterial inhibition activities of experimental groups 4 to 8 toward *Staphylococcus aureus* as determined by densitometry. Table 4 shows the bacterial inhibition activities of experimental groups 4 to 8 toward *Staphylococcus aureus* as determined by the colony-forming unit counting experiments. As shown in Table 3 and Table 4, the bacterial inhibition activities of the mouthwash compositions of experimental groups 4 and 5 are comparable to those of the commercially available products A, B, and C containing irritant chemicals, i.e., all higher than 95%.

TABLE 3

| Experimental group | 4 | 5 | 6 | 7 | 8 |
|---|---|---|---|---|---|
| Bacterial inhibition activity (%) | 98.58 | 99.29 | 95.64 | 96.62 | 95.91 |

TABLE 4

| Experimental group | 4 | 5 | 6 | 7 | 8 |
|---|---|---|---|---|---|
| Bacterial inhibition activity (%) | 99.99 | 99.99 | 99.99 | 99.99 | 99.99 |

Figure 3A:
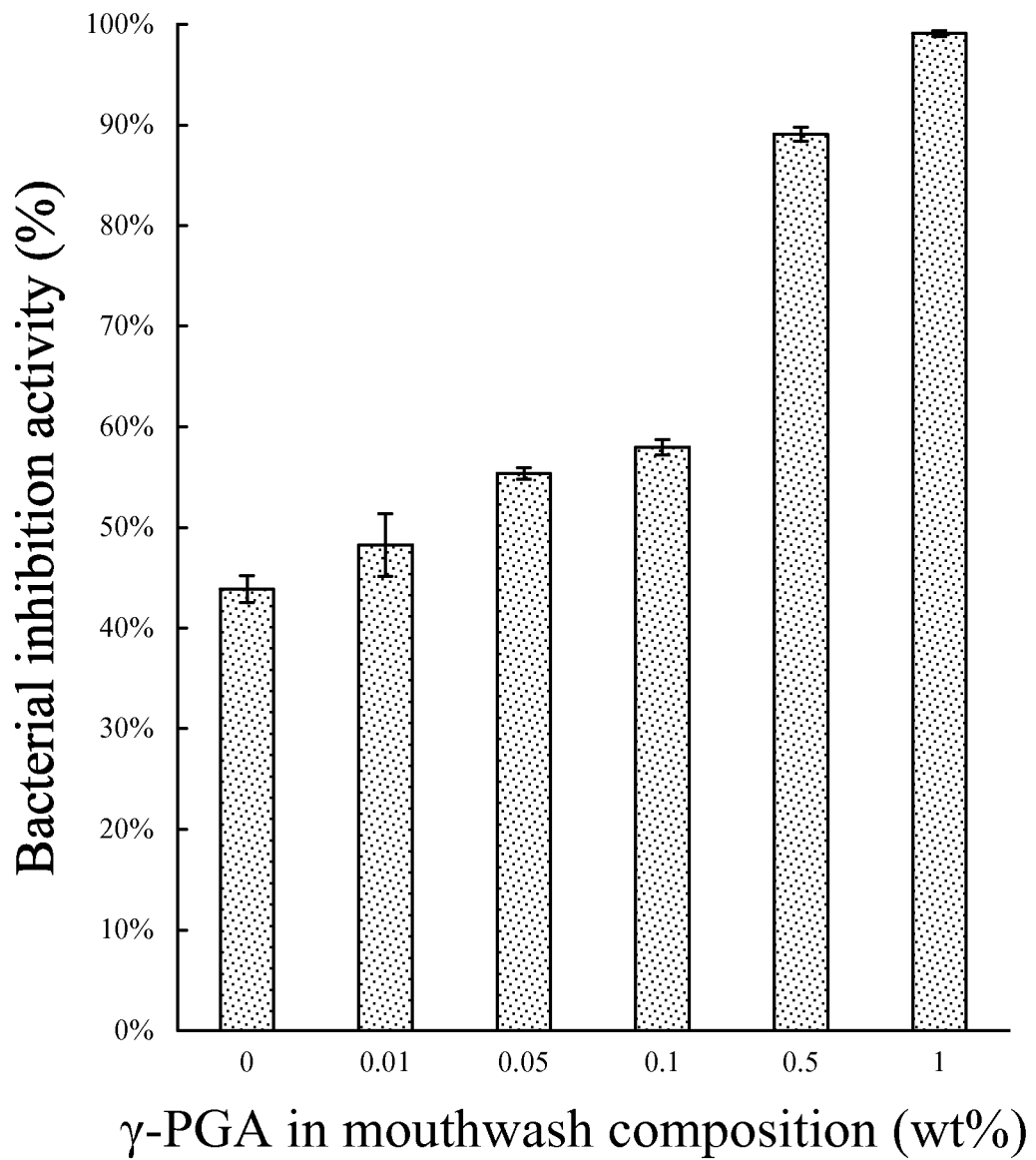
FIG. 3A is a bar chart based on densitometric measurements, showing the bacterial inhibition activities of the mouthwash compositions in an embodiment of the present invention, wherein the mouthwash compositions have different concentrations of γ-PGA and are reacted with *Pseudomonas aeruginosa*.
Figure 3B:
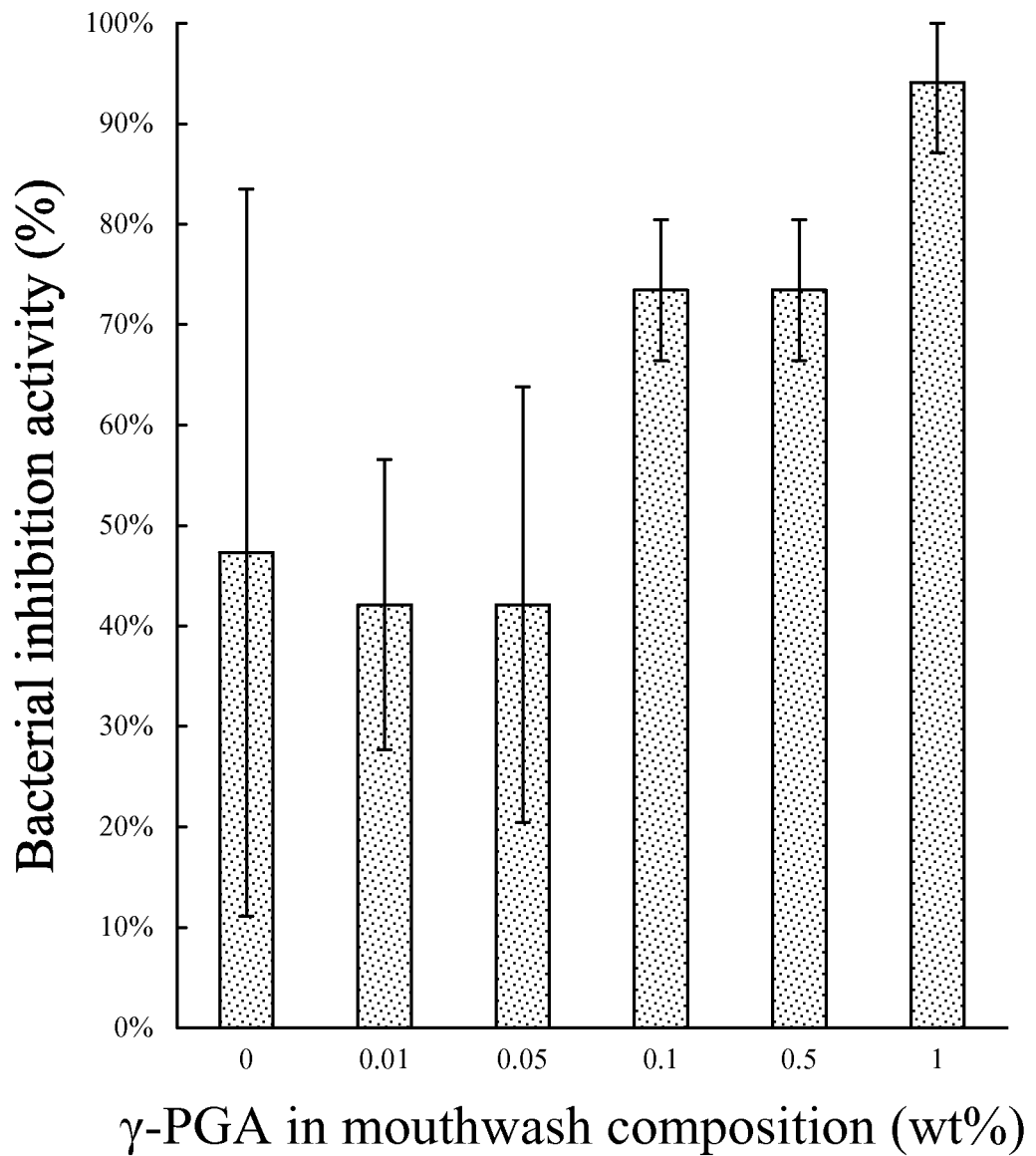
FIG. 3B is a bar chart based on the results of colony-forming unit counting experiments, showing the bacterial inhibition activities of the mouthwash compositions in an embodiment of the present invention, wherein the mouthwash compositions have different concentrations of γ-PGA and are reacted with *Pseudomonas aeruginosa*.

Reference is now made to FIG. 3A and FIG. 3B for the experiment results with regard to *Pseudomonas aeruginosa*. Both the densitometric measurements and colony-forming unit counting experiments show that, among the five non-alcohol mouthwash compositions without chemical antibacterial medicament (experimental groups 1~5), the mouthwash composition of experimental group 5 (containing 1 wt % of γ-PGA) exhibited a higher than 90% bacterial inhibition activity.

Table 5 shows the bacterial inhibition activities of experimental groups 4 to 8 toward *Pseudomonas aeruginosa* as determined by densitometry. Table 6 shows the bacterial inhibition activities of experimental groups 4 to 8 toward *Pseudomonas aeruginosa* as determined by the colony-forming unit counting experiments. As shown in Table 5 and Table 6, the bacterial inhibition activity of the mouthwash composition of experimental group 5 is comparable to those of the commercially available products A, B, and C containing irritant chemicals, i.e., all higher than 90%.

TABLE 5

| Experimental group | 4 | 5 | 6 | 7 | 8 |
|---|---|---|---|---|---|
| Bacterial inhibition activity (%) | 89.41 | 99.63 | 97.41 | 97.30 | 96.98 |

TABLE 6

| Experimental group | 4 | 5 | 6 | 7 | 8 |
|---|---|---|---|---|---|
| Bacterial inhibition activity (%) | 73.68 | 94.74 | 99.99 | 99.99 | 99.99 |

As stated above, the non-alcohol mouthwash composition without chemical antibacterial medicament in the aforesaid embodiment of the present invention includes from 0.03% to 1.5% by weight of γ-PGA, and the foregoing test results have shown the following: when γ-PGA makes up a relatively low percentage (e.g., 0.05%) of the total weight of the mouthwash composition, the mouthwash composition can inhibit the growth of only *Staphylococcus aureus*; when γ-PGA makes up a relatively moderate percentage (e.g., 0.5%) of the total weight of the mouthwash composition, the mouthwash composition can inhibit the growth of both *Staphylococcus aureus* and *Escherichia coli*; and when γ-PGA makes up a relatively high percentage (e.g., 1%) of the total weight of the mouthwash composition, the mouthwash composition can inhibit the growth of *Staphylococcus aureus, Escherichia coli*, and *Pseudomonas aeruginosa*. It can be known from the above that γ-PGA constituting from 0.8% to 1.3% of the total weight of the mouthwash composition can function as a substitute for, and inhibit bacterial growth as effectively as, the commonly used but irritant chemical compositions in commercially available mouthwash compositions.

The foregoing embodiments are illustrative of the characteristics of the present invention so as to enable a person skilled in the art to understand the contents disclosed herein and implement the present invention accordingly. The embodiments, however, are not intended to restrict the scope of the present invention, which is defined only by the appended claims. Hence, all equivalent modifications and changes which do no depart from the spirit of the present invention should be encompassed by the claims.

What is claimed is:

1. A non-alcohol mouthwash composition without chemical antibacterial medicament, consisting essentially of:
    γ-polyglutamic acid (γ-PGA) making up from 0.8% to 1.3% of a total weight of the mouthwash composition; and
    glycerol as a surfactant making up from 2% to 3% of the total weight of the mouthwash composition.

2. The mouthwash composition of claim 1, wherein the surfactant comprises glycerol in a concentration ranging from 95% to 99% by weight of the surfactant.

3. The mouthwash composition of claim 1, further comprising a perfume making up from 0.05% to 0.3% of the total weight of the mouthwash composition.

4. The mouthwash composition of claim 3, wherein the perfume is a spearmint essential oil, a peppermint essential oil, or a combination of both.

5. The mouthwash composition of claim 4, wherein the spearmint essential oil makes up from 0.1% to 0.2% of the total weight of the mouthwash composition.

* * * * *